(12) United States Patent
Loozen

(10) Patent No.: US 7,868,193 B2
(45) Date of Patent: Jan. 11, 2011

(54) 16,17-CARBOCYCLIC CONDENSED STEROID COMPOUNDS HAVING SELECTIVE ESTROGENIC ACTIVITY

(75) Inventor: Hubert Jan Jozef Loozen, Uden (NL)

(73) Assignee: N.V. Organon, Oss (NL)

( * ) Notice: Subject to any disclaimer, the term of this patent is extended or adjusted under 35 U.S.C. 154(b) by 321 days.

(21) Appl. No.: 10/297,706

(22) PCT Filed: May 1, 2001

(86) PCT No.: PCT/EP01/04868

§ 371 (c)(1),
(2), (4) Date: Dec. 6, 2002

(87) PCT Pub. No.: WO02/00682

PCT Pub. Date: Jan. 3, 2002

(65) Prior Publication Data

US 2004/0102426 A1     May 27, 2004

(30) Foreign Application Priority Data

Jun. 6, 2000    (EP)  .................................. 00201986

(51) Int. Cl.
     *C07J 1/00*        (2006.01)
     *A61K 31/56*     (2006.01)

(52) U.S. Cl. ........................ 552/502; 552/514; 514/169; 514/178; 514/182

(58) Field of Classification Search ................ 514/841, 514/169, 178, 179, 182; 552/502, 514
See application file for complete search history.

(56) References Cited

U.S. PATENT DOCUMENTS 3,194,821 A     7/1965    Freiberg et al.

FOREIGN PATENT DOCUMENTS

EP        0798378 A      10/1997
EP        0 869 132        10/1998

OTHER PUBLICATIONS

J.R. Bull et al: "Synthesis of 14, 17-Propano analogues of estradiol"; Journal of the Chemical Society, Perkin Transactions1., 1997, pp. 1179-1192.
El Garrouj Driss et al: "Steroidal affinity labels of the estrogen receptor: 1. 17-alpha-(Bromoacetoxy)alky/alkynylestradiols."; Journal of Medicinal Chemistry, vol. 36, No. 20, 1993, pp. 2973-2983.
Mosselman, et al., "ERβ: Identification and Characterization of a Novel Human Estrogen Receptor," *FEBS Letters*, 392, 1996, pp. 49-53.
Wronski, T.J., et al., "The Ovariectomised Rat as an Animal Model for Postmenopausal Bone Loss," *Cells and Materials*, Supp. 1, 1991, pp. 69-74.
Yamazaki, I. et al., "Characteristics of an Ovariectomised Osteopenic Rat Model," *J. Bone Min. Res.* 4, 1989, pp. 13-22.
Ederveen, A.G.H., et al., "Tibolone, a Steroid with a Tissue-Specific Hormonal Profile, Completely Prevents Ovariectomy-Induced Bone Loss in Sexually Mature Rats," *J. Bone Min. Res.* vol. 14, 1999, pp. 1963-1970.
Allen, E. et al., "An Ovarian Hormone," *J. Amer. Med. Assoc.*, 81, 1923, pp. 819-821.

*Primary Examiner*—Sreeni Padmanabhan
*Assistant Examiner*—Shobha Kantamneni
(74) *Attorney, Agent, or Firm*—Susan L. Hess; Valerie J. Camara

(57) ABSTRACT

The invention discloses a steroid compound having the formula (1), wherein dotted bonds represent optional double bonds; $R_6$ is H, $=CH_2$, or $-CH_3$, or $-CH_2-CH_3$; $R_7$ is H, $C_{1-4}$-alkyl, $C_{2-5}$ alkenyl or $C_{2-5}$-alkynyl, wherein the alkyl, alkenyl or alkynyl group may be substituted with 1 to 3 halogen atoms independently chosen from the group of fluorine or chlorine atoms; $R_{11}$ is H, $C_{1-4}$-alkyl, $C_{2-4}$-alkenyl, $C_{2-4}$-alkynyl or $C_{1-4}$-alkylidene, wherein the alkyl, alkenyl, alkynyl or alkylidene group may be substituted with 1-3 halogen atoms independently chosen from the group of fluorine or chlorine atoms; E represents together with carbon atoms 16 and 17 of the steroid skeleton a four to seven-membered ring, said ring being α and in cis-configuration with respect to the steroid skeleton, optionally comprising one or two endocyclic bonds; or a prodrug thereof. Such compounds can be used in therapy and for methods for selective modification of the activity of estrogen receptors.

(1)

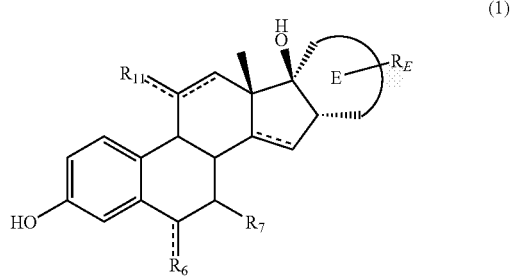

4 Claims, No Drawings

16,17-CARBOCYCLIC CONDENSED STEROID COMPOUNDS HAVING SELECTIVE ESTROGENIC ACTIVITY

FIELD OF THE INVENTION

The present invention relates to steroid compounds with an additional E ring connected to ring D of the steroid skeleton having estrogenic activity.

BACKGROUND OF THE INVENTION

There is continued interest in new compounds with affinity for the estrogen receptor. This stems from the discovery of two distinct subtypes of receptors, denoted ERα and ERβ (see Mosselman et al., *FEBS Letters* 392 (1996) 49-53 as well as EP-A-0 798 378). Compounds which are selective for such subtypes of receptors make it possible to provide a more selective estrogen-receptor related treatment. Advantages can for example be obtained from the different distribution of receptor subtypes in human tissue. This enables treatments with a lower burden of estrogen-related side-effects. Examples of estrogen-related medical treatments which can benefit from selective compounds are those for contraception, for therapy of menopausal complaints, osteoporosis, and estrogen dependent tumour control.

DETAILED DESCRIPTION OF THE INVENTION

In EP 0 869 132 estrogenic steroid compounds are described which have the formula (1):

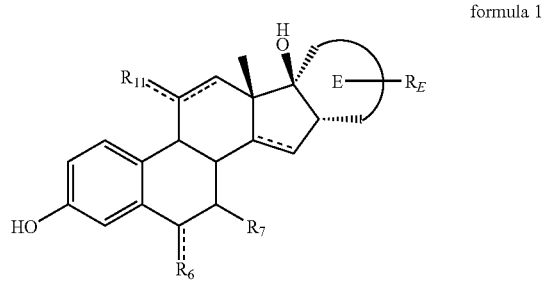

formula 1 wherein:
  dotted bonds represent optional double bonds;
  $R_6$ is H, =$CH_2$, or —$CH_3$, or —$CH_2$—$CH_3$;
  $R_7$ is H, $C_{1-4}$-alkyl, $C_{2-5}$ alkenyl or $C_{2-5}$-alkynyl, wherein the alkyl, alkenyl or alkynyl group may be substituted with 1 to 3 halogen atoms independently chosen from the group of fluorine or chlorine atoms;
  $R_{11}$ is H, $C_{1-4}$-alkyl, $C_{2-4}$-alkenyl, $C_{2-4}$-alkynyl or $C_{1-4}$-alkylidene, wherein the alkyl, alkenyl, alkynyl or alkylidene group may be substituted with 1 to 3 halogen atoms independently chosen from the group of fluorine or chlorine atoms;
  E represents together with carbon atoms 16 and 17 of the steroid skeleton a four to seven-membered ring, said ring being α in cis-configuration with respect to the steroid skeleton, optionally comprising one or two endocyclic bonds and substituted with $R_E$, which has a variety of meanings.

It was further disclosed in EP 0 869 132 that any alkyl, alkenyl, alkynyl and alkylidene group in the steroid compound having the formula (I) may be branched or unbranched. If $R_6$ or $R_{11}$ is connected to the steroid skeleton through a single bond, the substituted carbon atom of the steroid skeleton either comprises a hydrogen atom or is involved in a double carbon-carbon bond. Compounds may contain different centres of chirality and can exist as enantiomers and diastereomers. Hydroxyl groups may be capped with substituents such as acyl or alkyl leading to prodrugs of a compound according to formula 1.

It is now found that a steroid compound having formula 1 with symbols and terms having the meanings as defined above, characterised in that $R_E$ is a β-hydroxy group, or a prodrug thereof, has, unexpectedly, a consistently better selectivity for the estrogen receptor α combined with a high estrogen α potency. Such a compound, hereafter referred to as a compound of the invention, usually is not only very weakly active on the estrogen receptor β, but in fact is generally an antagonist on the estrogen receptor β, which contributes to the very high selectivity for the estrogen receptor α and furthermore enables a selective treatment based on blockade of the estrogen receptor β. The compounds of this invention include the aforementioned enantiomers and diastereomers within its scope and each of the individual (R) and (S) enantiomers, substantially free, i.e. associated with less than 5%, preferably less than 2%, in particular less than 1% of the other enantiomer and mixtures of such enantiomers in any proportions including racemic mixtures containing substantially equal amounts of the two enantiomers.

A preferred embodiment of the invention is a steroid compound as defined previously and further characterised in that $R_6$ is H, $R_7$ is a branched or unbranched $C_{1-3}$-alkyl, the E-ring is a five or six-membered ring without double bonds having a hydroxy at position 22 in S stereoconfiguration, which configuration in other words is β with respect to the steroid skeleton according to the meaning common in steroid stereochemistry notification.

Most preferred is the compound according to formula 2, which is (7α, 16β, 17α, 22S)-7-propyl-16,24-cyclo-19,21-dinorchola-1,3,5(10)-triene-3,17,22-triol, having the code name Org 41621:

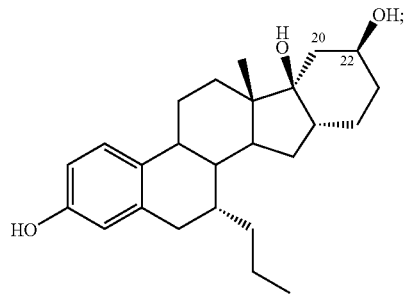

Formula 2

Org 41621

Compounds according to this invention enable therefore a more directed, in other words selective modification of the activity of estrogen α or β receptors in an organism.

A prodrug is defined as being a compound which converts in the body of a recipient to a compound according to formula 1 with $R_E$ being a β-hydroxyl group. Notably, the hydroxy groups at position 3, 17 and on the E-ring can for example be converted into ethers (alkyl*oxy) or esters such as acyl*oxy, phosphate, sulfate, sulfonate or aromatic carboxylate, whereby the carbon chain length of the groups denoted with an asterisk (*) is not considered to be sharply delimited. An acyl group is derived from a linear or branched alkane* and an aromatic carboxylate generally will comprise a phenyl, pyridinyl or pyrimidyl. The length of the alkyl and acyl groups is selected depending on the desired properties of the prodrugs, whereby the longer chained prodrugs with for example lauryl or caproyl chains are more suitable for sustained release and depot preparations. It is known that such substituents spontaneously hydrolyse or are enzymatically hydrolysed to the free hydroxyl substituents on the skeleton of the compound. Such prodrugs will have biological activity comparable to the compounds to which they are converted in the body of the recipients. The active compound to which a prodrug is converted is called the parent compound. The onset of action and duration of action as well as the distribution in the body of a prodrug may differ from such properties of the parent compound.

Both for medical therapies as well as for physiological, medical and pharmacological experiments such selective compounds as found now are desperately needed. It is an aspect of the invention that a compound of the invention can be used for therapy by administering the compound to a recipient, being human or an animal, preferably a mammal. The different distribution of α and β receptors over different tissues of an organism provides targets for more selective interference with the functioning of different tissues. It is known that species dependent, estrogen receptors α are expressed predominantly in vaginal tissue and liver tissue, whereas β receptors are expressed predominantly in prostate tissue, the epithelial cell layer of rat bladder, vascular endothelial smooth muscle cells and certain brain regions, such as the basal forebrain, neocortex and hippocampus. Tissues wherein both receptors are present are for example the pituitary, hypothalamus, thymus, uterus, ovary and bone.

The estrogen-receptor affinity profile of the compounds of the present invention, makes them suitable as improved estrogens or anti-estrogens under diminished estrogen-related side-effects. Thus, the invention discloses a method for selective modification of the activity of estrogen receptors by bringing a compound of the invention into contact with estrogen receptors. Such a method can be a treatment of the human or animal body, but it can also be a non-medical method. The latter method can be an experimental method, such as an assay for selective compounds or an in vitro laboratory method to obtain information on estrogen receptors or compounds interacting therewith. Preferably, these compounds can be used for selective estrogen-receptor α or β related contraceptive, experimental, or medical treatments, such as those for treatment or prevention of estrogen receptor related disorders, menopausal complaints, osteoporosis, cardiovascular disorders, modulation of pituitary hormone regulation, benign prostate hypertrophy, estrogen dependent tumour control, colon cancer, endometriosis or central nervous system disorders. An important common characteristic of these selective methods and treatments is that these comprise the bringing of a compound of the invention into contact with estrogen receptors.

The invention also relates to the use of a compound according to the invention for the manufacture of a medicament for selective estrogen receptor related treatment and of a medicament for treatment of estrogen receptor α related disorders, comprising the administration to a patient of a compound according to the invention (in a suitable pharmaceutical dosage form). In view of the antagonistic effect of a compound according to the invention on the estrogen receptor β the invention also provides for the manufacture of a medicament for treatment of estrogen receptor β related disorders, comprising the administration to a patient of a compound according to the invention (in a suitable pharmaceutical dosage form).

Further, the invention relates to the use of a compound according to the invention in the manufacture of a medicament having contraceptive activity. Thus the invention also pertains to the medical indication of contraception, i.e. a method of contraception comprising the administration to a subject, being a woman or a female animal, of a progestogen and an estrogen as is customary in the field, wherein the estrogen is a compound according to this invention (in a suitable pharmaceutical dosage form).

Finally the invention relates to the use of a compound according to the invention for the manufacture of a medicament having selective estrogenic activity, such a medicament being generally suitable in the area of HRT (hormone replacement therapy) having a menopausal complaints relieving, in particular, an anti-osteoporose activity.

The dosage amounts of the present compounds will be of the normal order for estrogen-related compounds, e.g. of the order of 0.01 to 100 mg per administration.

To this end dosage units can be prepared containing amounts of a compound of the invention in the same order of magnitude as the above indicated treatment doses. Therefore, the present invention also relates to a pharmaceutical composition comprising a compound of the invention mixed with one or more pharmaceutically acceptable auxiliaries.

The compounds of the invention may be produced by various methods known in the art of organic chemistry in general, and especially in the art of the chemistry of steroids. See for example: Fried, J. and Edwards, J. A., "*Organic Reactions in Steroid Chemistry*", Volumes I and II, Van Nostrand Reinhold Company, New York, 1972; and C. Djerassi, "Steroid Reactions", Holden-Day, Inc., San Francisco, 1963.

For the synthesis of a compound according to the invention steroids with an additional 16,17 anellated ring have to be synthesised. Methods to do so have been described in EP 0 869 132. For the compounds of this invention an additional hydroxy function must be introduced on the anellated ring. For this purpose it is convenient to carry out the anellation reaction in such a way that suitably located double bonds result from the synthetic procedure, for example by using a well known olefin metathesis procedure, whereby transition metal catalysts are used which are derived from e.g. ruthenium, molybdenum, or tungsten, to close a 16α, 17α-bis unsaturated fragment into an unsaturated anellated 5- or 6 membered ring. The olefin ring thus synthesised is first stereoselectively epoxidized. This can be done generally with agents like peracids (preferably in a buffered medium) or catalytic systems using metal complexes in the presence of oxidizing agents (like hydrogen peroxide or t-butylhydroperoxide). In the present cases perbenzoic acid with sodiumbicarbonate buffer generally gives good results. The epoxides can be almost regioselectively reductively opened with hydride reagents to the required beta-alcohols. Hydroxy groups may be easily synthesised as well by application of a hydroboration/oxidation procedure.

In cases where the α-hydroxy compounds are obtained, a Mitsunobu inversion easily leads to the β-alcohols, which are the intended ones.

The hydroxy compounds can be converted into prodrugs, such as alkyl ethers, acyl esters, carbonates, sulphonates or phosphates, by reaction with the appropriate alkyl halide or acid chloride as desired.

A pharmaceutical composition comprising one or more compounds according to the invention can be prepared with or without combination with pharmaceutically acceptable auxiliaries, such as described in the standard reference Gennaro et al., *Remmington's Pharmaceutical Sciences*, (18th ed., Mack publishing Company, 1990, see especially Part 8: Pharmaceutical Preparations and Their Manufacture.). A mixture of one or more compounds according to the invention and one or more pharmaceutically acceptable auxiliaries may be compressed into solid dosage units, such as pills or tablets, or be processed into capsules or suppositories. By means of pharmaceutically suitable liquids the compounds can also be applied as an injection preparation in the form of a solution, suspension, emulsion, or as a spray, e.g. nasal spray. The compounds of the invention may also be included in an implant, a vaginal ring, a patch, a gel, and any other preparation for sustained release. For making dosage units, e.g. tablets, the use of conventional additives such as fillers or carriers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof used in suitable amounts.

EXAMPLES

The routes of synthesis used in the examples are illustrated in the schemes I and II. The numbers used to identify the compounds are defined by the structural formulas in these schemes.

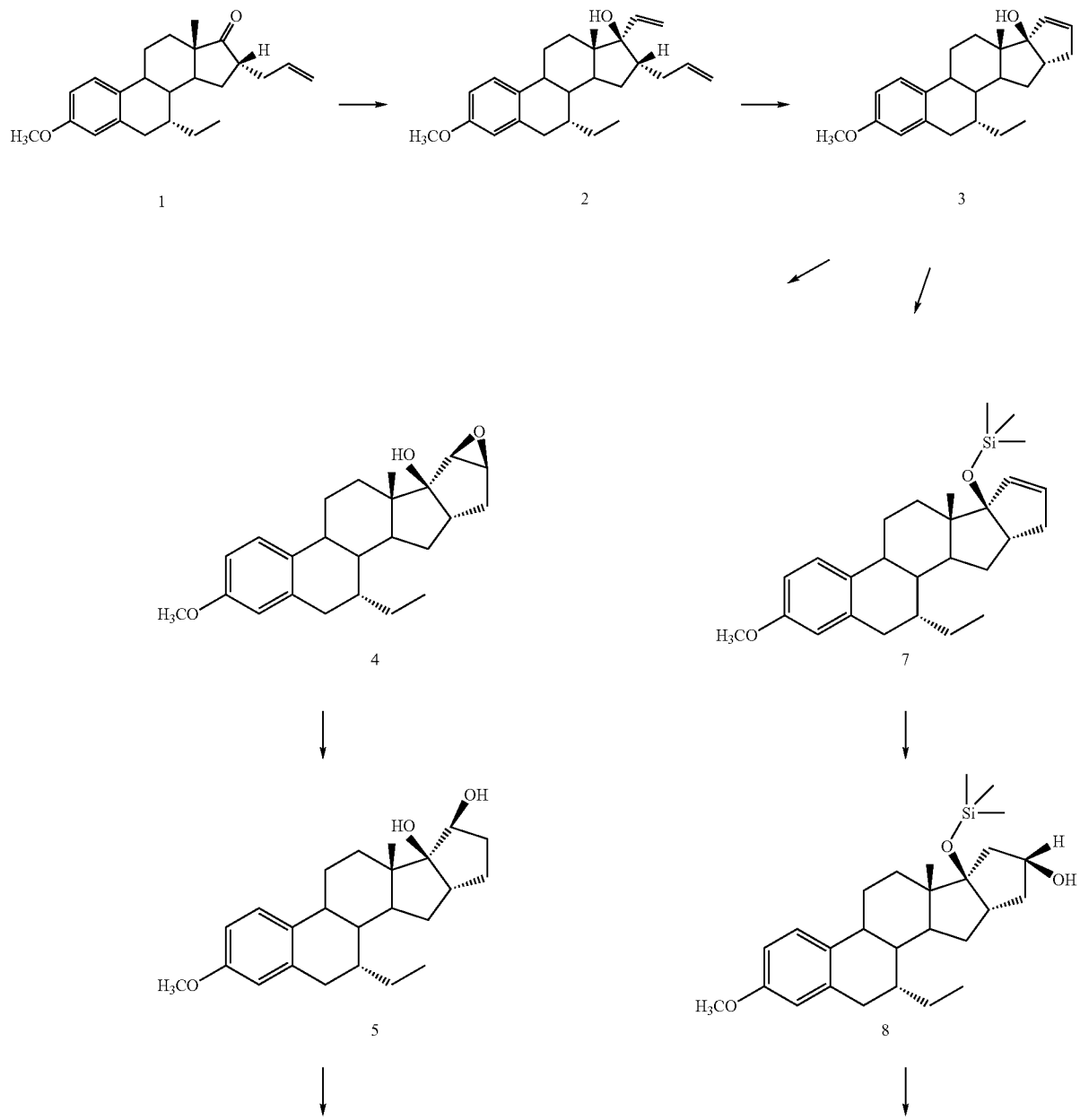

-continued
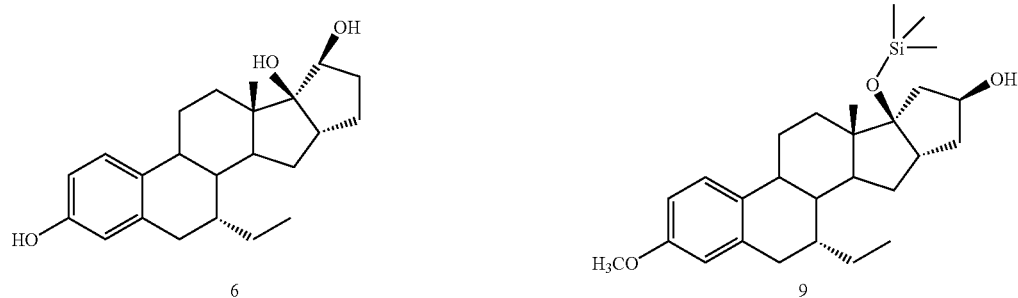
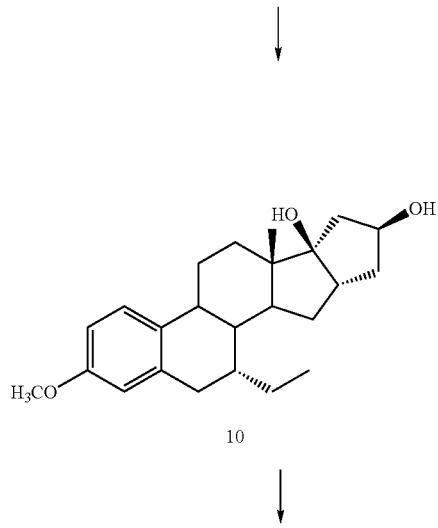
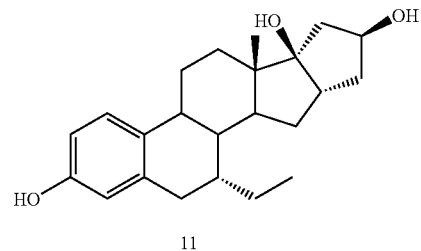
SCHEME II
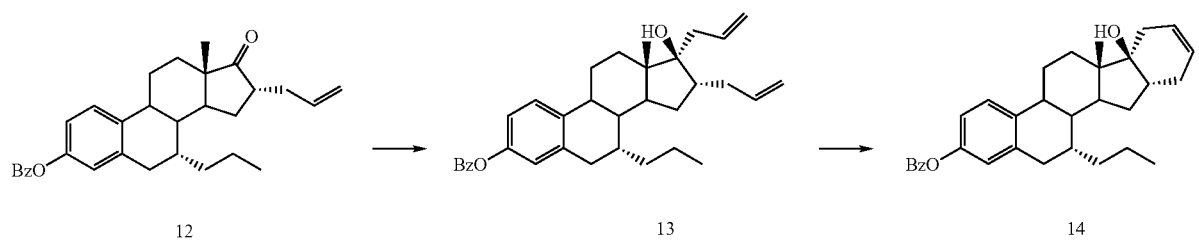

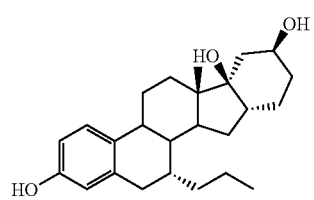 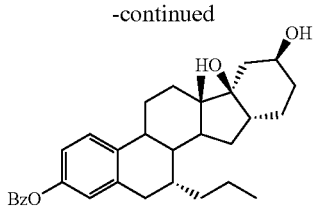 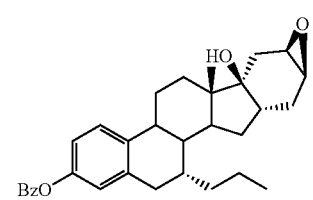

17  16  15

Compound 2

To a solution of 5.65 ml of vinyltributyltin in 50 ml of dry THF was added at −50° C. dropwise 12 ml of 1.6 M BuLi in hexane. After stirring for an additional 0.5 hr a solution of 6.2 gr of 16α-allyl,7α-ethylestrone-3-O-methylether (1) in 20 ml of dry THF was added at −50° C. Upon stirring for an additional ½ h the mixture was poured into sat.NH$_4$Cl and extracted with ethylacetate. Concentration of the organic phase followed by silicagel chromatography gave 4.2 g of 2 as an oil, $R_f$ 0.47 (toluene/ethyl acetate 95/5), for 1 $R_f$ 0.65. NMR (CDCl$_3$) δ 5.80 (m, 1, CH allyl), 6.07 (m, 1, CH vinyl) 0.98 (s, CH$_3$), 0.93 (t, 3, ethyl), 3.78 (s, 3, CH$_3$).

Compound 3

To a solution of 4.2 g of 2 in 80 ml of methylenechloride was added 0.32 g of benzylidenetriscyclohexylphosphinoruthenium dichloride (Grubbs metathesis catalyst). After stirring for 1 hr an additional portion of 0.3 g of catalyst was added. After completion of the reaction (2 h) the mixture was concentrated and the residue purified by column chromatography, to provide 3.5 g of 3, $R_f$ 0.29 (heptane/ethyl acetate 8/2, for 2 $R_f$ 0.55). NMR (CDCl$_3$) δ 5.72 (m, CH=) 6.02 (m, 1, C=) 0.99 (s, 3, CH$_3$), 0.89 (t, 3, CH3) 3.77 (OCH$_3$) 0.92 (m, 3, CH$_3$).

Compound 4

A mixture of 0.4 g of steroid 3 and 0.5 g of NaHCO$_3$ in 12 ml of methylenechloride was treated with 0.34 g of m-Cl-perbenzoic acid. After stirring for several hours at ambient temperature the reaction was diluted with water, and treated with sodiumthiosulphate solution to destroy residual peroxide. The organic material was extracted into ethyl acetate and finally purified by chromatography, to provide 110 mg of the desired β-epoxide 4; $R_f$ 0.50 (toluene-acetone 9/1); NMR (CDCl$_3$) δ 0.98 (t, 3, CH$_3$), 0.92 (t, 3, CH$_3$), 3.65+3.70 (2×m, epoxide CH's).

Compound 5

A solution of 80 mg of steroid 4 in 3 ml of THF was refluxed with 10 mg of LiAlH$_4$. After 2 h starting material had disappeared. The mixture was quenched by addition of 30 μl of sat. Na$_2$SO$_4$ solution and 0.20 g of Na$_2$SO$_4$, stirred for 15 min and filtered over Celite. The filtrate was concentrated and the residue passed over a short silica column, to give 55 mg of 5; $R_f$ 0.24 (toluene-acetone 9/1); NMR(CDCl$_3$) δ 4.04 (m, 1, CHOH), 3.78 (s, 3, OCH$_3$) 2.85 (m, 2, CH$_2$ at C6), 0.92 (s, 3, CH$_3$).

Compound 6

To a solution of sodiumethanethiolate (prepared from 0.7 ml of ethanethiol and 0.27 g of a 60% NaH dispersion) in 9 ml of DMF was added 120 mg of steroid 5. The mixture was refluxed for 3 h. Then the reaction was poured into water and extracted with ethyl acetate. Chromatography of the organic material provided 80 mg of 6, Mp 224-226; $R_f$ 0.30 (toluene-acetone 8/2); NMR(CDCl$_3$) δ 4.00 (m, 1, CHOH), 7.12 (ar H1), 6.20 (ar H2), 6.54 (ar H4).

Compound 7

To a solution of 2.7 g of steroid 3 in 20 ml of methylenechloride and 3 ml of pyridine, was added at 0° C. 1.9 ml of trimethylsilylchloride. After stirring for ½ h the reaction was poured into water and extracted with ethyl acetate, to provide 3.3 g of essentially pure silyloxy derivative 7, $R_f$ 0.8 (heptane-acetone 8/2); NMR(CDCl$_3$) δ 0.03 (s, 9, TMS), 5.68, 5.91 (2×s, CH olefin).

Compound 8

A solution of 3.2 g of 7 in 25 ml of dry THF was treated at 0° C. with a solution of 2.2 ml borane-dimethylsulfide complex in 20 ml of THF. The reaction was subsequently stirred for 2 hr at 45° C. Excess reagent was destroyed by careful addition of 4.5 ml of abs.ethanol, followed by 11 ml of 2N NaOH and 7.7 ml of 30% hydrogenperoxide. The reaction was stirred overnight, diluted with water and extracted with ethyl acetate. The crude product thus obtained was purified by column chromatography and yielded 1.7 g of the desired α-alcohol 8. $R_f$ 0.36 (heptane-acetone 8/2); NMR(CDCl$_3$) δ 4.42 (m, 1, CHOH), 0.12 (s, 9, TMS), 0.79 (s, 3, CH3).

Compound 9

A solution of 1.6 g of 8 and 1.3 g of triphenylphosphine in 60 ml of toluene was treated with 0.84 g of p-nitrobenzoic acid and 0.8 ml of diethylazodicarboxylate at 0° C. After stirring for 1 h the reaction was complete. The mixture was poured onto sat.aq. NaHCO$_3$ solution and extracted with ethyl acetate. Chromatografic purification gave 2.9 g of β-nitrobenzoate, $R_f$ 0.64 (heptane-acetone 8/2); NMR(CDCl$_3$) δ 5.34 (m, 1, CHOC(O)Ar), 0.91 (s, 3, CH$_3$), 0.95 (t, 3, CH$_3$), 3.80 (s, 3, OCH$_3$). This material was dissolved in a mixture of 40 ml of THF-methanol (1/1 v/v) and treated with 4 ml of 2N NaOH solution. After stirring for 15 min the reaction was poured into water and the product extracted into ethyl acetate. After passing through a short silica column 1.3 g of β-alcohol 9 was obtained. $R_f$ 0.64 (heptane-acetone 8/2); NMR(CDCl$_3$) δ 4.31 (m, 1, CHOH).

Compound 10

A solution of 1.3 g of 9 in 30 ml of acetone was treated with 2 ml of 2N HCl. After 1 h the mixture was neutralized by addition of saturated NaHCO$_3$ and concentrated. The residue was diluted with water and extracted with ethyl acetate, to provide 1.0 g of 10, $R_f$ 0.10 (heptane-acetone 8/2); NMR (CDCl$_3$) δ 0.90 (t, 3, CH$_3$) 0.95 (s, 3, CH$_3$), 4.48 (m, 1, CHOH).

Compound 11

To a solution of sodiumethanethiolate (prepared from 0.7 ml of ethanethiol and 0.3 g of a 60% NaH dispersion) in 9 ml of DMF was added 120 mg of steroid 10. The mixture was refluxed for 3 h. Then the reaction was poured into water and extracted with ethyl acetate. Chromatography of the organic material provided 80 mg of 11, Mp 143-145° C. (ethanol-water); $R_f$ 0.41 (toluene-acetone 7/3); NMR(CDCl$_3$) δ 4.45 (m, 1, CHOH), 0.93 (s, 3, CH$_3$) 0.90 (t, 3, CH$_3$), 6.62+7.10 (AB, 2, H1, 2), 6.53 (d, 1, H4).

Compound 13

To a solution of 29 ml of 1M allylmagnesium bromide in ether was added 80 ml of dry THF. At −50° C. was added 10 gr of 7α-propyl, 16α-allylestrone-3-O-benzylether 12 in 40 ml of THF. After stirring for ½ h the mixture was allowed to come to room temperature and poured into 300 ml of sat aq NH$_4$Cl. The product was extracted with ethyl acetate and purified, by chromatography over silica gel to remove stereoisomers providing 7.2 g of the desired 16α,17α-diallyl derivative 13. $R_f$ 0.26 (heptane-ethylacetate 9/1); 17β-allyl isomer $R_f$ 0.45. NMR(CDCl$_3$) δ 0.88 (t, 3, CH$_3$), 0.96 (s, 3, CH$_3$), 6.08 (m, 1, CH allyl), 5.80 (m, 1, CH allyl), 4.95-5.20 (m, 4, 2× CH$_2$ allyl) 5.02 (CH$_2$OBz).

Compound 14

A portion of 40 mg of benzylidenetriscyclohexylphosphinoruthenium dichloride (Grubbs metathesis catalyst) was added to a solution of 450 mg of 13 in 10 ml of methylenechloride. After stirring for 1 h an additional 400 mg of catalyst were added. After 2 h, the solvent was removed and replaced by 20 ml of toluene and the mixture was stirred with 5 g of basic alumina at 60° C. to absorb the catalyst. After filtration over Celite and washing with toluene and ethyl acetate, 400 mg of almost pure 14 was obtained; $R_f$ 0.34 (heptane-ethylacetate 8/2); $R_f$ 13 0.45. NMR(CDCl$_3$) δ 0.02 (s, 2, CH$_2$O), 5.97 (s, 2, CH=CH), 0.97 (s, 3, CH$_3$)

Compound 15

To a solution of 340 mg of 14 in 0.5 ml of methylenechloride was added 8 μl of pyridine, 0.14 ml of 30% aq H$_2$O$_2$, followed by 2 mg of methyltrioxorhenium. After stirring for 1 h the epoxidation was complete, leading predominently to the desired β-epoxide as well as some α-isomer. The mixture was poured onto water and sat. Na$_2$S$_2$O$_3$ and extracted with ethylacetate. Chromatography provided 230 mg of 15 and 80 mg of the undesired α-epoxide. $R_f$ 0.36 (toluene-ethylacetate 95/5; for reference: $R_f$ compound 14: 0.39). NMR(CDCl$_3$) δ 3.31, 3.38 (m, 2, CH(O)CH).

Compound 16

A mixture of 4.2 g of 15 and 350 mg of LiAlH$_4$ in 20 ml of dry THF was refluxed for 2 h. Then the mixture was cooled and subsequently treated with 1 ml of sat aq. Na$_2$SO$_4$, 28 ml of ethyl acetate and 8 g of Na$_2$SO$_4$. After stirring for ½ h at ambient temperature the reaction was filtered over Celite and the filtrate concentrated and chromatographed, to provide 3.4 g of 16, Mp 147-148° C., $R_f$ 0.20 (toluene-ethylacetate 8/2; $R_f$ 23 0.55). NMR(CDCl$_3$) δ 4.25 (broad s, 1, CHOH), 0.90 (s, 3, CH$_3$), 0.86 (t, 3, CH$_3$), 5.02 (s, 2, OCH$_2$Ar).

Compound 17; (=7α, 16β, 17α, 22S)-7-propyl-16,24-cyclo-19,21-dinorchola-1,3,5(10)-triene-3,17,22-triol A solution of 3.3 g of 16 in 200 ml of ethanol was hydrogenated in the presence of 300 mg of 5% Pd/C. After completion of the reaction the catalyst was filtered over Celite, and the solvent concentrated. The residue was triturated with ether, and then with water, to provide 1.7 g of 17; Mp 146-147° C., $R_f$ 0.53 (toluene-ethylacetate 1/1; $R_f$ 16 0.60). NMR (CDCl$_3$) δ 4.26 (broad s, 1, CHOH) 7.14, 6.62 AB, 2, H1, H2), 6.54 (d, H4).

Tests for Estrogenic Activity In Vitro

Compounds are tested for their estrogen receptor activity in a binding assay and in a transactivation assay using the human estrogen receptor α or β.

Competitive binding to cytoplasmic human estrogen receptor α or β from recombinant Chinese hamster ovary (CHO) cells is used to estimate the relative binding affinity (=RBA)(potency ratio) of a test compound as compared with (17β)-estradiol (E$_2$) for estrogen receptors α or β present in the cytosol of recombinant CHO cells, stably transfected with the human estrogen receptor α (hERα) or β receptor (hERβ).

The estrogenic and antiestrogenic activity of compounds is determined in an in vitro bioassay with recombinant Chinese hamster ovary (CHO) cells stably co-transfected with the human estrogen receptor α (hERα) or β (hERβ), the rat oxytocin promoter (RO) and the luciferase reporter gene (LUC). The estrogenic agonistic transactivation (potency ratio) of a test compound to stimulate the transactivation of the enzyme luciferase mediated via the estrogen receptors hERα or hERβ is compared with the standard estrogen estradiol. The antiestrogenic activity (potency ratio) of a test compound to inhibit the transactivation of the enzyme luciferase mediated via the estrogen receptors hERα or hERβ by the (17β)-estradiol is compared with the standard ICI 164.384 (=(7α,17β)-N-butyl-3,17-dihydroxy-N-methylestra-1,3,5 (10)-triene-7-undecanamide).

Results:

Formula 3

| Compound as Form. 3 | $R_7$ | $R_{11}$ | 6-ring (n = 1) or 5-ring (n = 0) | Binding-assay Erα/Erβ | Trans-activation Erα/Erβ | Agonist selectivity Erα/Erβ |
|---|---|---|---|---|---|---|
| A | H | H | 6-ring | 8.6/0.3 | 5.5/0.2 | 27 |
| B | CH$_3$ | H | 6-ring | 20/5.2 | 16/<0.1 | >160 |
| C(=11) | C$_2$H$_5$ | H | 5-ring | 18/14 | 12/<0.1 | >120 |
| D | C$_2$H$_5$ | H | 6-ring | 17/8.7 | 11.5/<0.1 | >115 |
| E(=17[1)] | C$_3$H$_7$ | H | 6-ring | 42/13.9 | 26/<0.1 | >260 |
| F | H | C$_3$H$_7$ | 5-ring | 16.3/0.4 | 11/0.2 | 55 |

[1)] 17 is Org 41621

Compound 17 has in the antagonist assays a selectivity ratio Erα/Erβ of <0.1/67.

A compound of the prior art according to formula 3, but without 22-hydroxy and having $R_7$ α-propyl, $R_{11}$ hydrogen and 6-membered E-ring, which is named (7α, 16β, 17α)-7-propyl-16,24-cyclo-19,21-dinorchola-1,3,5(10)-triene-3,17-diol, has a ERα/ERβ ratio in the binding assay of 15/7 and in the agonist transactivation assay 0.3/<0.1.

Test for Prevention of Ovariectomy-Induced Bone Loss in Rats (Anti-Osteoporosis Test).

Introduction

Ovariectomy of rats induces bone loss, which is due to estrogen deficiency. Administration of estrogenic compounds prevents this effect. The test is used to evaluate a compound for anti-osteoporotic activity in ovariectomised (OVX) rats.

The effect on bone mass can be evaluated by peripheral Quantitative Computed Tomography (pQCT), or by quantitative analysis of X-ray pictures. Plasma osteocalcin and urinary deoxypyridinoline, calcium and phosphate gives information on bone metabolism. Increase of uterine weight and decrease of body and thymus weight reflect estrogenic effect.

Test Animal

Mature virgin 225-250 g female Wistar rats. Strain: Hsd/Cpd:Wu, SPF-bred by Harlan, CPB, Zeist, The Netherlands.

Experiment

On day 1 of the experiment the rats are weighed and distributed over the cages in order of bodyweight, whereby the rat with the smallest bodyweight is placed in the first cage and the heaviest rat in the final cage. Treatments are randomised over the rats.

Sham-operation and ovariectomy are performed under ether anaesthesia. After recovery from the anaesthesia, within 24 h, vehicle, reference compound or test compound is administered once or twice daily for 4 weeks. During this period the rats are weighed weekly. After 4 weeks autopsy was performed. At autopsy the rats are anaesthetised with ether and blood is collected from the abdominal aorta. Both femora, the vertebrae L1L2L3L4 (optionally), uterus, thymus, liver, kidneys, adrenals, thyroid, and pituitary gland are dissected out. Measurement of bone mineral density and geometry of the right femur is performed by pQCT on the day of autopsy on fresh tissue. Trabecular bone mineral density of the metaphyseal part of the femur (FBMDDIS mg/cm$^3$) is measured with a pQCT (peripheral Quantitative Computed Tomography machine; XCT 960A, Stratec, Birkenfeld, Germany).

Interpretation of Results

Ovariectomy causes a statistically significant decrease in distal bone density and trabecular bone volume of the femur and a statistically significant increase in plasma osteocalcin and urinary deoxypyridinoline levels ($P \leq 0.05$, 2 way ANOVA).

Test compounds are considered to be active when mean bone density values of the distal femur are significantly increased as compared to the ovariectomised control group. Effects of compounds on urinary deoxypyridinoline levels reflects an effect on bone resorption, effects on plasma osteocalcin levels reflects an effect on bone turnover and may help to understand the mechanism of action.

The minimal active dose (MAD) is the dose where a mean proportional difference in trabecular bone mineral density between 40 and 60% is reached.

REFERENCES

Wronski T. J. and Yen C. F.: The ovariectomised rat as an animal model for postmenopausal bone loss. Cells and Materials, Supp. 1 (1991): 69-76.

Yamazald I. and Yamaguchi H.: Characteristics of an ovariectomised osteopenic rat model. J. Bone Min. Res. 4 (1989): 12-22.

Ederveen A. G. H. and Kloosterboer H. J.: Tibolone, a steroid with a tissue-specific hormonal profile, completely prevents ovariectomy-induced bone loss in sexually mature rats. J. Bone & Mineral Research Vol 14, pp 1963-1970, 1999.

Result:

Compound 17 (Org 41621): Osteoporosis test oral 30 µg/kg. Prior art compound (7α, 16β, 17α)-7-propyl-16,24-cyclo-19,21-dinorchola-1,3,5(10)-triene-3,17-diol: 190 µg/kg per oral.

Test for Strogenic Activity In Vivo

In vivo estrogenic activity was determined by means of the Allen Doisy test, described in F. Allen, L. A. Doisy, J. Amer. Med. Assoc., 81, 819-821 (1923)

Result:

Compound 17 (Org 41621): Allen Doisy sc 5 µg/kg, oral 30 µg/kg. Prior art compound (7α, 16β, 17α)-7-propyl-16,24-cyclo-19,21-dinorchola-1,3,5(10)-triene-3,17-diol: Allen Doisy sc 24 µg/kg, oral 125 µg/kg.

The invention claimed is:

1. A compound according to formula 2:

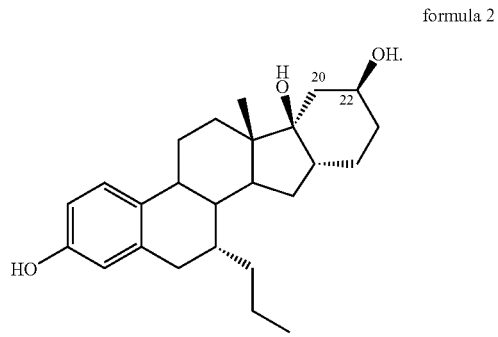

formula 2

2. A steroid compound having formula 1:

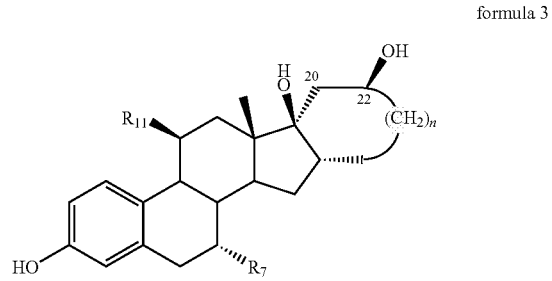

formula 3 wherein $R_7$ is H, $R_{11}$ is $C_3H_7$ and n is 0.

3. A pharmaceutical composition, comprising:
the steroid compound according to claim 1 and a pharmaceutically acceptable auxiliary.

4. A pharmaceutical composition, comprising:
the steroid compound according to claim 2 and a pharmaceutically acceptable auxiliary.

* * * * *